United States Patent
Wang et al.

(10) Patent No.: US 11,154,571 B2
(45) Date of Patent: Oct. 26, 2021

(54) EXOSOMES SOURCED FROM GRANULOCYTIC MYELOID-DERIVED SUPPRESSOR CELLS AND APPLICATION THEREOF

(71) Applicant: Jiangsu University, Jiangsu (CN)

(72) Inventors: Shengjun Wang, Jiangsu (CN); Yungang Wang, Jiangsu (CN); Jie Tian, Jiangsu (CN); Ke Rui, Jiangsu (CN); Jie Ma, Jiangsu (CN); Bin Ma, Jiangsu (CN); Xinyi Tang, Jiangsu (CN); Huaxi Xu, Jiangsu (CN)

(73) Assignee: JIANGSU UNIVERSITY, Jiangsu (CN)

( * ) Notice: Subject to any disclaimer, the term of this patent is extended or adjusted under 35 U.S.C. 154(b) by 442 days.

(21) Appl. No.: 15/507,838

(22) PCT Filed: Apr. 30, 2015

(86) PCT No.: PCT/CN2015/077902
§ 371 (c)(1),
(2) Date: Mar. 1, 2017

(87) PCT Pub. No.: WO2016/127503
PCT Pub. Date: Aug. 18, 2016

(65) Prior Publication Data
US 2018/0078581 A1    Mar. 22, 2018

(30) Foreign Application Priority Data
Feb. 12, 2015 (CN) .................. 201510072238.X

(51) Int. Cl.
*A61K 35/15* (2015.01)
*C12N 5/09* (2010.01)
*C12N 5/0783* (2010.01)

(52) U.S. Cl.
CPC ............ *A61K 35/15* (2013.01); *C12N 5/0637* (2013.01); *C12N 5/0693* (2013.01)

(58) Field of Classification Search
None
See application file for complete search history.

(56) References Cited

U.S. PATENT DOCUMENTS

| | | | |
|---|---|---|---|
| 2006/0116321 A1* | 6/2006 | Robbins ................. | A61K 35/16 424/85.2 |
| 2008/0305079 A1* | 12/2008 | Chen ..................... | A61K 35/28 424/85.2 |
| 2012/0237587 A1* | 9/2012 | Wehling .................. | A61P 19/08 424/450 |
| 2015/0190430 A1 | 7/2015 | Lim | |

FOREIGN PATENT DOCUMENTS

| | | |
|---|---|---|
| CN | 103626846 A | 3/2014 |
| CN | 104127438 A | 11/2014 |
| CN | 104673749 A | 6/2015 |
| WO | 2012149416 A | 11/2012 |

OTHER PUBLICATIONS

Burke et al., published Dec. 2013, Prot. Res. vol. 13: 836-843.*
Zoller et al., 2018, Frontiers Immunol. vol. 9: 1-21.*
Crook et al., 2014, WOrld J. Immunol. vol. 4: 26-33.*
Zhu et al., 2018, BioMed Res. INt. pp. 1-12.*
Zhang et al., 2018, PNAS, vol. 115: E6927-6936.*
Yang, Xiaojun, "Prolongation of Rat Intestinal Recipients' Survival by Administration of exsomes derived from Donor Immature Dendritic Cells", Medicine 7 Public Health, China Doctoral Dissertations Full-Text Database, E059-22, Jul. 15, 2011, ISSN: ISSN 1674-022X.

* cited by examiner

Primary Examiner — Amy E Juedes
(74) Attorney, Agent, or Firm — Miller Law Group, PLLC

(57) ABSTRACT

Provided are exosomes sourced from a granulocyte myeloid-derived suppressor cell and an application thereof. The exosomes are named as G-MDSC exo. Also provided is a use of the exosomes in preparing a drug used for suppressing autoimmune diseases. The G-MDSC exo can effectively suppress proliferation of CD4+T cells in vitro, promote induced proliferation of T regulatory (Treg) cells, alleviate foot swelling of model mice having delayed-type hypersensitivity, and suppress attacks of inflammatory bowel disease (IBD) and collagen-induced arthritis (CIA) of the mice.

7 Claims, 4 Drawing Sheets

EXOSOMES SOURCED FROM GRANULOCYTIC MYELOID-DERIVED SUPPRESSOR CELLS AND APPLICATION THEREOF

FIELD OF INVENTION

This invention relates to granulocytic-like myeloid-derived suppressor cells derived exosomes (G-MDSC exo) and application thereof, which belongs to the fields of cell biology, molecular biology and clinical application. Specifically, the present invention relates to the preparation of G-MDSC exo from spleens of tumor-bearing mouse, the research of biological function and its application in treatment of murine autoimmune diseases.

BACKGROUND OF THE INVENTION

Myeloid-derived suppressor cells (MDSCs) are myeloid-derived heterogeneous cells that proliferate greatly under pathological cases of tumor, inflammation and pathogen infection (Gabrilovich D I, Nagaraj S. Myeloid-derived suppressor cells as regulators of the immune system. Nat Rev Immunol. 2009; 9(3):162-74.). MDSCs of mouse are Gr-1 (consisting of Ly6G and Ly6C markers) and CD11b double-positive cells. Two subtypes of MDSCs can be divided into by cell morphology and the expression level of Ly6G and Ly6C: $CD11b^+Ly6G^+Ly6C^{low}$ granulocytic like MDSCs (G-MDSCs), and $CD11b^+Ly6G^-Ly6C^{hi}$ monocyte like MDSCs (M-MDSCs). Both subtypes expand greatly under conditions such as tumor and infection, and the expansion of G-MDSCs is significantly more than that of M-MDSCs. G-MDSCs inhibit T cell-mediated adaptive immune responses and natural anti-tumor immune responses mediated by natural killer cells (NK) and macrophage through expressing arginase 1 (Arg-1) and reactive oxygen species (ROS). Studies have shown that MDSCs can induce regulatory T cells (Tregs) differentiation through interferon γ (IFN-γ) and interleukin 10 (IL-10) dependent-pathway thereby down-regulating function of effector T cells. In recent years, studies show that MDSCs have great potential in the treatment of autoimmune diseases. Therefore, the therapeutic value of MDSCs is re-evaluated. MDSCs have been used to treat mouse collagen-induced arthritis (CIA) and showed some efficacy. However, the lack of sources, inconvenience of storage and complex composition limit its application.

Autoimmune diseases are caused by immune system responding to their own constituents, which have a high morbidity in the population. Inflammatory bowel disease (IBD) is a non-specific, inflammatory intestinal disease which is mainly caused by the abnormal immune response to the normal flora which is at tolerable state. IBD includes ulcerative colitis (UC) and Crohn's disease (CD). The main clinical symptoms are abdominal pain, diarrhea, and bloody mucopurulent stools; long term illness may lead to the development of cancer. Rheumatoid arthritis (RA) is a common clinical systemic autoimmune disease, the main clinical symptoms include symmetry small joint lesion, characterized by persistent inflammation in multiple joints. Large amount of studies have shown that proinflammatory Th1 and Th17 cells and their derived inflammatory factors play important roles in the development of autoimmune diseases. Tregs play an essential role in maintaining the intestinal immune balance. The imbalance of Tregs function is one of the causes of autoimmune diseases. Studies confirmed that the number of Tregs in patients with autoimmune diseases is lower than healthy persons. In recent years, the incidence of autoimmune diseases is on the rise in China. However, autoimmune diseases patients mainly receive symptomatic treatment in clinic, but there is no effective treatment measures, thus exploring an effective and curative treatment method is urgently desirable.

Exosomes are membranous vesicles released into extracellular environment after fusion of intracellular multivesicular complete with the plasma membrane. It has been demonstrated that almost all living cells can secrete exosomes, and exosomes widely exist in various body fluids (Beninson L A, M. Fleshner. Exosomes: an emerging factor in stress-induced immunomodulation[J]. Semin Immunol, 2014. 26(5): 394-401). Exosomes carry protein, mRNA and miRNA and other ingredients derived from the derived cells, and protect them from degradation by the external environment, and are beneficial to their biological function of active ingredients. Exosomes can be internalized by receptor cells through giant pinocytosis, lipid rafts and receptor-mediated endocytosis etc. and the internalized exosomes can regulate and control multiple biological function of receptor cells and play an important role in intercellular communication. The roles of exosomes in the process of immune response, apoptosis, angiogenesis, inflammation reaction, and tumor occurrence and development have been reported. Studies showed that exosomes exhibited more advantages than derived cells when they were used in disease intervention. It had been reported that dendritic cell-derived exosomes were used to treat cancer and showed good efficacy (Pitt J M, Charrier M, Viaud S, et al. Dendritic cell-derived exosomes as immunotherapies in the fight against cancer [J]. J Immunol, 2014; 193(3):1006-11.). However, studies on function of G-MDSC exo and the application thereof in the treatment of autoimmune diseases have not been reported.

We found that G-MDSC exo has a diameters of 40-100 nm, carries biologically active ingredients and the biological characters were clearer than other G-MDSC secreted vesicles. G-MDSC exo could suppress $CD4^+$ T cell proliferation, relieve the foot pad swelling degree of Delayed Type Hypersensitivity (DTH) mouse, and promote the expansion of $CD4^+$ T cell to Tregs induced by TGF-β. Application of G-MDSC exo in vivo could attenuate the severity of DTH response, IBD and CIA, and further demonstrating that this function depends on Arg-1 carried by G-MDSC exo at certain degree.

In recent years, researches on exosomes in disease treatment mainly concentrated on dendritic cells and stem cells derived exosomes. In the aspect of disease treatment, exosomes exhibit more advantages than derived cells. Firstly, storage and transport of exosomes are easier, has no cytotoxicity, and they can be used with less biosafety problems. Secondly, the complex molecules on the surface of exosomes offer potential homing mechanisms for specific target tissues and microenvironments (Xinrui Tian, Wenqing Tian, Bo Niu, et al. The preparation of neural stem cells derived exosomes and application thereof in the nervous system diseases. China, CN103740645 A[P].2014-04-23). Lastly, exosomes protect the therapeutic proteins and nucleic acids, thereby reducing degradation of the therapeutic proteins and nucleic acids (Marcus M E, Leonard J N. FedExosomes: Engineering Therapeutic Biological Nanoparticles that Truly Deliver W. Pharmaceuticals (Basel), 2013, 6(5):659-680.). The application of G-MDSC exo in the treatment of disease has not been reported. Our experimental results showed that G-MDSC exo could maintain the biological activity for a long time at low temperatures. G-MDSC exo not only could suppress $CD4^+$ T cell proliferation similar to G-MDSC but also could promote the expansion of CD4+ T cell to Tregs cell induced by TGF-β. G-MDSC exo is a natural immunomodulator, is essential in the treatment of autoimmune diseases and has good application value in clinic.

Based on structural and functional properties of G-MDSC exo, the application of G-MDSC exo in the treatment of autoimmune diseases will achieve the purpose of "low-input, high output". It has a good prospect of clinical application, is expected to play a positive role in maintaining the body's immune balance. It will provide a new therapeutic approach for autoimmune disease.

SUMMARY OF THE INVENTION

This invention is to overcome the deficiencies in the prior art, and provides G-MDSCs derived exosomes (G-MDSC exo). This exosomes have nonspecific components of G-MDSCs and specific active components such as protein and nucleic acid in G-MDSCs, is a composite informosomes of subcellular structure. G-MDSC exo not only possess immunosuppressive properties of G-MDSCs and but also contains its own surface molecule CD63. We have observed its role in the therapy of autoimmune diseases to seek method to treat disease fundamentally.

G-MDSC exo of the present invention are membranous vesicles composed of derived cell membrane lipid components, which has protection effects on their carried bioactive ingredients. G-MDSC exo can play immunosuppressive roles similar to G-MDSCs, and the exosomes have many advantages that G-MDSCs do not have, they are composite informosomes of subcellular structure for intercellular information transmission.

The invention discloses a simple method to prepare G-MDSC exo derived from tumors or autoimmune disease individuals. The whole process is short time-consuming, high yield. G-MDSC exo is easy for storage and has stable biological activity. This method provides the basis for massive production of G-MDSC exo for therapeutic purposes. Briefly, we constructed mouse tumor or autoimmune disease models (e.g. CIA), isolated G-MDSCs from spleens, collected culture supernatants, and finally extracted G-MDSC exo with combination of ultracentrifugation centrifugation and microporous membrane filter.

The detailed procedures are as follows:

The collected G-MDSCs culture suspension was centrifuged at 4° C. and then collected the supernate, repeating 3 times. The supernatant fraction was transferred to MWCO 100 kDa ultrafiltration centrifuge tube, and then collect the concentrated solution in the tube after centrifugation. The concentrated solution was mixed with ExoQuick-TC™ Exosome reagent (v/v=5:1), vibrated and stewed at 4° C., the supernatant was discarded after centrifugation at 4° C., collecting the sediment to obtain exosomes.

G-MDSC exo in the present invention suppress T cell proliferation and promote Tregs polarization. Application of G-MDSC exo in vivo may play strong immunosuppressive role and is essential in the therapy of autoimmune diseases.

G-MDSC exo in the present invention could effectively alleviate clinical development of DTH, IBD and CIA in mouse, reducing pathological damage. The present invention provides a novel pathway to treat autoimmune diseases by restoring the immune balance.

This invention also confirmed that G-MDSC exo exhibited the immunosuppressive effects by inhibiting CD4+ T cell proliferation and promoting Treg cell expansion. G-MDSC exo plays a protective effect on autoimmune diseases and provides a new approach for the treatment of autoimmune diseases.

It is an advantage that the present invention prepares G-MDSC exo from tumors or autoimmune disease individuals, and it lays the foundation for its application and associated biological function investigation.

It is another advantage, compared with the conventional differential centrifugation, the process of preparing G-MDSC exo in the present invention is short time-consuming, simple, convenient for large scale extraction, and the structure of G-MDSC exo is complete.

In is another advantage that the active ingredients contained in G-MDSC exo are stable and easy to preserve, when stored at −80° C. it can preserve for more than one year. At room temperature, the structure and activity of G-MDSC exo are stable, and they are easy to transport without cryopreservation and resuscitation. All these advantages provide a technical basis for the clinical application of G-MDSC exo.

It is still another advantage that G-MDSC exo is a nano-grade composite informosomes of subcellular structure without cytotoxicity, has a high clinical safety.

It is yet another advantage that G-MDSC exo has a therapeutic effect on autoimmune diseases, its preparation and application provides a new way for the treatment of autoimmune diseases.

It is a further advantage that G-MDSC exo inhibits CD4+ T cell proliferation and promotes Treg expansion, it provides a new concept for the treatment of autoimmune diseases.

Figure 1:
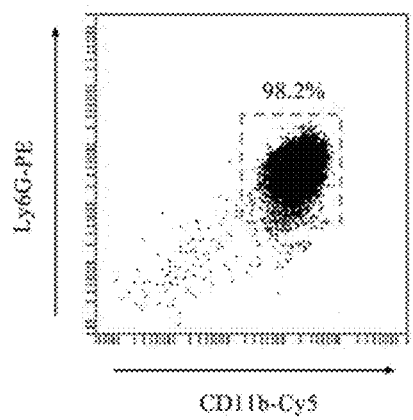
FIG. 1: Purity of G-MDSCs sorted by immune magnetic beads and detected by fluorescence activated cell sorter (FACS) analysis.

B: Effect of G-MDSC exo on the disease progression of IBD mouse after inhibiting the activity of Arg-1; C: Effect of G-MDSC exo on the colon tissues of IBD mouse after inhibiting the activity of Arg-1; D: Effect of G-MDSC exo on the colonic inflammation after inhibiting the activity of Arg-1.

DETAILED DESCRIPTION OF THE PREFERRED EMBODIMENTS

The technical solutions of this invention are described in conjunction with specific embodiments as follows but the invention is not limited to these embodiments.

Example 1: G-MDSCs Sorting and the Preparation of Culture Supernatant (1) The model of tumor-bearing mouse was established with the Lewis lung adenocarcinoma cell line (LLC): Lewis lung adenocarcinoma cells were cultivated in an incubator at 37° C. and 5% $CO_2$ in the medium (DMED with pH 7.2 and 10% fetal bovine serum). When the cell density is about 85% of the petri dish bottom area, cells are digested with 0.25% trypsin. Male 6-8 w C57BL/6 mouse were subcutaneously injected at the right side of the abdomen in a dose of $3.0 \times 10^6$ cells per mouse in logarithmic growth phase. The growth of tumors was observed after tumor planting.

(2) Establishment of CIA model: An equal volume of bovine collagen type II (C II) and complete Freund's adjuvant are mixed at a ratio of 1:1 and grind until the mixture is completely emulsified, The degree is that dropping the emulsion into water and it is not loose (operation in ice-bath). Emulsified C II (0.1 mL/mouse) was injected intradermally in the base of the tail and make the emulsion to be absorbed completely. Using the emulsion of C II and incomplete Freund's adjuvant strengthen the immune at day 21 after immunization, the day to immune is designated as day 0.

(3) Isolation of splenocytes from tumor-bearing mouse or CIA mouse: After the model is constructed, mouse were sacrificed by eye bloodletting, then the spleen was sterilely removed and grinded in 0.22 μm sieve. The suspension was filtered and centrifuged at 4° C., 500 g for 5 min, the supernatant was discarded, and 5 mL of ACK lysis buffer is added into the cell pellet and mix well to lyse erythrocytes therein, hold for 5 min, and then add RPMI-1640 culture solution to 10 mL. Lastly, the cell suspension was centrifuged at 4° C., 500 g for 5 min, and the number of cells was calculated.

(4) G-MDSCs were isolated by magnetic bead: Splenocytes were resuspended in 350 μL of PBE buffer per $10^8$ total cells, then 50 μL of FcR blocking reagent was added, mixing well and incubate for 10 minutes on the ice; adding anti-Ly-6G-Biotin (40 μL/$10^8$ splenocytes), mixing well and incubate for 30 minutes on the ice, mixing every 10 minutes; adding 10 mL of PBE buffer and centrifuge at 500 g for 5 minutes at 4° C., discarding the supernatant; adding anti-Ly-6G-Biotin beads (50 μL/$10^8$ splenocytes), mixing well and incubate for 30 minutes on the ice, mixing every 10 minutes; adding 10 mL of PBE buffer and centrifuge at 500 g for 5 minutes at 4° C., discarding the supernatant; adding 500 μL of PBE buffer and mixing well; placing MACS sorting column on VarioMACS separator, rinsing the sorting column with 3 mL of PBE buffer; adding cell suspension onto the sorting column, washing column with 9 mL of PBE buffer for 3 times after the first drop of the suspension outflows, removing the column from the separator and adding 5 mL of PBE onto the column, pushing column bolt, squeezing out the cells bonding to the column, collecting the cell suspension. Then, G-MDSCs were acquired.

(5) Purity analysis of G-MDSCs: $1 \times 10^6$ G-MDSCs were collected in EP tubes and resuspended with 1 mL of PBS, and the cell suspension was centrifuged at 4° C., 500 g for 5 min. The supernatant was discarded, 100 μL PBS were left and resuspended, adding 0.5 μL of anti-Ly-6G antibody and 0.5 μL anti-CD11b antibody and incubating at 4° C. for 30 min, and then resuspending with 1 mL of PBS, centrifuging at 4° C., 500 g for 5 min, discarding the supernatant and then adding 200 μL of PBS to resuspend. The expression of cell surface molecules detected by FACS, and the results was showed in FIG. 1. G-MDSCs are CD11b and Ly-6G double-positive cells. The present invention uses immune magnetic beads to sort G-MDSCs from tumor-bearing mouse spleen. The purity of G-MDSC was detected by FACS, and the purity of MDSCs was >95%.

(6) Preparation of the culture supernatant of G-MDSCs: The sorted G-MDSCs were resuspended in RPMI-1640 culture solution containing 10% of fetal bovine serum (that had been ultra-centrifuged at 100,000 g for 16 h), inoculating onto 24-well plate at $1.5 \times 10^6$ per well, the total volume is 1 ml per well, incubating at 37° C. and 5% $CO_2$ for 24 h. The culture supernatant of G-MDSC was harvested by centrifuging at 4° C., 300 g for 20 min.

Example 2: Preparation of G-MDSC Exo and Detecting of Protein Concentration (1) The harvested G-MDSCs supernatant was centrifuged at 4° C., 1000 g for 30 min, the supernatant was collected and centrifuged at 4° C., 10000 g for 30 min. The supernatant was transferred to an ultrafiltration centrifugal tube with MWCO 100 kDa and was centrifuged at 1500 g for 30 min, and the concentrated liquid in the tube was collected.

(2) G-MDSC exo was extracted by ExoQuick-TC™ Exosome Kit purchased from SBI as follows: The concentrated liquid collected in step (1) was mixed with ExoQuick-TC™ Exosome reagent (v/v=5:1), the mixture was vibrated and followed with a standing at 4° C. for more than 12 h and centrifuged at 4° C., 1000 g for 30 min, the precipitate was G-MDSC exo. G-MDSC exo was dissolved in PBS, dispensed to EP tube, and stored at −80° C. for subsequent testing.

(3) Determine the protein concentration of G-MDSC exo by using the BCA Protein Assay Kit: The G-MDSC exo suspension was mixed with the lysis buffer (RIPA: PMSF=250:1) at equivalent volume and incubated for 1 h on ice, shake it every 10 min Finally, the mixture was centrifuged at 4° C., 12000 g for 15 min, and the supernatant was collected. The protein concentration in the lytic exosomes supernatant was detected according to the manufacture's instructions.

Figure 2:
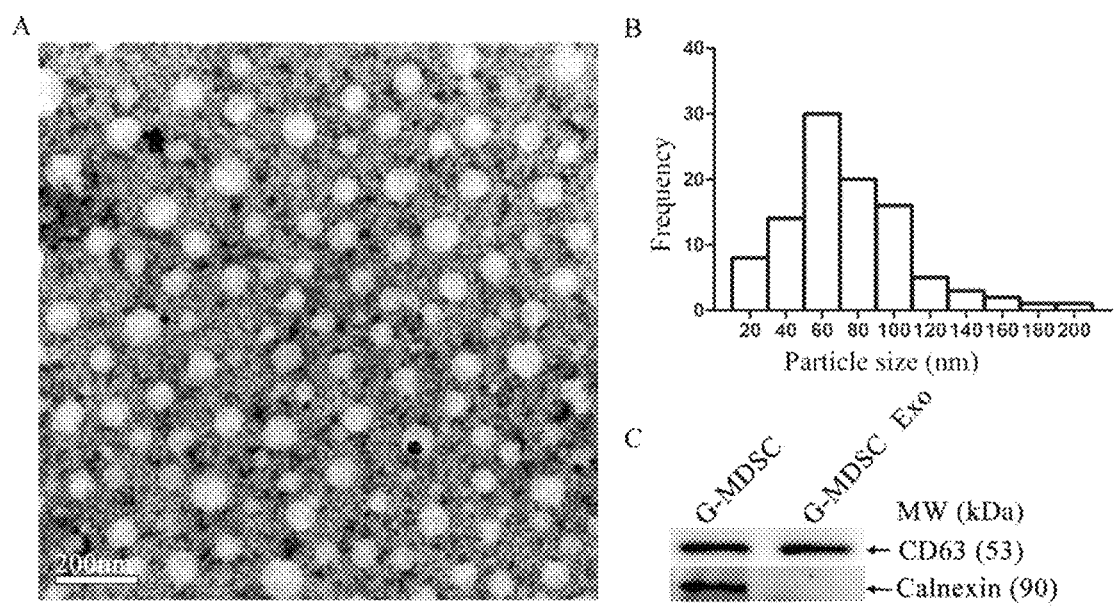
FIG. 2: Identification of G-MDSC exo. A: Morphology of G-MDSC exo; B: Particle-size and frequency distribution of G-MDSC exo; C: Expression of G-MDSC exo detected by western blot.

Example 3: Identification of G-MDSC Exo (1) Observing the morphology of G-MDSC exo through transmission electron microscopic: 20 μL of G-MDSC exo suspension were dropped on a 3 mm diameter of sample loading copper mesh, and rest for 2 minutes at room temperature; using filter paper to sip up the liquid gently, and drop 2% of phosphotungstic acid at pH 6.8 on the copper mesh and negatively staining for 1 min, using filter paper sip up the dye liquid and dried under incandescent light bulb. G-MDSC exo were observed as circular or elliptic microcapsule structure having envelope by transmission electron microscopy, and the intracavity has low electron density components with particle size of 30-150 nm. The result is showed in FIGS. 2A and 2B. FIG. 2A shows the morphology of G-MDSC exo, the G-MDSC exo were observed as circular or elliptic micro-capsule structure having complete envelope by transmission electron microscopy, and the intracavity has low electron density components. FIG. 2B shows the frequency of particle-size distribution of G-MDSC exo. The particle size of G-MDSC exo observed by transmission electron microscope is distributed at the range of 30-150 nm.

(2) The detection of CD63 molecules contained in exosomes and proteins Calnexin contained in mitochondria by Western blot: preparing 5% of spacer gel and 12% of separation gel, the denatured G-MDSC exo was loaded at 250 μg. After 100V constant voltage electrophoresis, and 350 mA constant current for 90 min, 5% defatted milk encloses the PVDF film for 1 h, and incubated with CD63 monoclonal antibody or calnexin monoclonal antibody overnight at 4° C. The PVDF membrane was washed with TBS/T for 10 min and repeated 3 times. Then the PVDF membrane was incubated with Horse Radish Peroxidase (HRP) conjugated anti-mouse second antibody for 30 min at 37° C. The PVDF membrane was washed with TBS/T for 10 min, repeated 3 times and exposed and developed with ImageQuant LAS 4000 gel imaging system, the result is as shown in FIG. 2C. In FIG. 2C, the western blot shows that G-MDSC exo express CD63 molecules and do not express mitochondria related calnexin molecules.

Example 4: G-MDSC Exo Suppress T Cell Proliferation and DTH Response (1) The effect of G-MDSC exo on $CD4^+$ T cell proliferation was detected with 3H-TdR incorporation method: $CD4^+$ T cells were isolated. 6-8 week male C57BL/6 mouse were sacrificed by breaking the neck. The spleen was removed and ground sterile, and splencytes suspension was prepared. The supernatant was discarded after being centrifuged at 4° C., 500 g, for 5 min. The cell sediment was added into 5 ml of ACK and stood for 5 min. Then 5 ml RPMI-1640 was added into suspension and centrifuging at 4° C., 500 g for 5 min. The precipitate was dissolved with 10 ml of PBE followed by centrifuging at 4° C., 500 g for 5 min and discarding the supernatant. 15 μl anti-CD4-MicroBeads was added into cells suspension at $1.0 \times 10^7$ $CD4^+$ T cell. The cells suspension was placed on the ice for 30 min and mixed every 10 minutes. 10 ml of PBE was added to wash cells and followed by centrifuging at 4° C., 500 g for 5 min and discarding the supernatant. 500 μl of PBE was added into the precipitation and cell suspension was prepared. Cell sorting column was put on the VarioMACS separator and rinsed with 3 ml of PBE. The cells suspension was added into cell sorting column and 9 ml of PBE was used to wash sorting column after the first drop of suspension outflows. The column is removed and 5 ml of PBE was added. Push the stud and collect the cell suspension flowed out from the sorting column $CD4^+$ T cells are obtained. $CD4^+$ T cells in 200 μl cell culture medium were inoculated into 96-well plate at $5 \times 10^5 CD4^+$ T cells per well. Under the presence of anti-CD3 mAb and anti-CD28 mAb, different doses of G-MDSC exo were added into the wells. Cells were cultured with RPMI-1640 culture solution at pH 7.2 which contains 10% fetal bovine serum (after 100000 g×16 h centrifugal) under 5% $CO_2$ atmosphere at 37° C. for 72 h, and $[^3H]$-thymidine (1 μCi/well) was added. After 16 h. the counts per minute (CPM) values of various wells were detected with an LS6500 Multi-Purpose Scintillation Counter.

(2) Observing inhibition effects of G-MDSC exo on $CD4^+$ T cells proliferation by mouse DTH model: DTH model was induced in 6-8 w male C57BL/6 mouse, the mice were divided into normal control group (NC), DTH group, Neu exo treatment group, G-MDSX exo treatment group, and 6 mouses per group. In brief, C57BL/6 mouse were first immunized by intradermal injections of 200 μl of CFA-emulsified OVA peptide at a final concentration of 1 mg/ml at the tail root and back. Seven days after immunization, each mouse was stimulated by right footpad injection of 30 μl of OVA peptide at a concentration of 20 mg/ml. Footpad thickness was measured at 24 h, 48 and 72 h after stimulating. The degree of footpad swelling in each group was calculated according to the judgment standard of DTH reaction. The result shows that degree of footpad swelling in G-MDSC exo treatment group is milder than the DTH group and Neu exo treatment group (FIG. 3B), and is statistically significant ($p<0.05$). These results implied that G-MDSC exo could suppress $CD4^+$ T cells in vivo.

The level of the DTH response was determined as follows (take 24 h for example):

Swelling degree of footpad=(footpad thickness after OVA injection for 24 h [min]–footpad thickness before OVA injection [mm])–(footpad thickness after PBS injection for 24 h [min]–footpad thickness before PBS injection [mm]).

Figure 3:
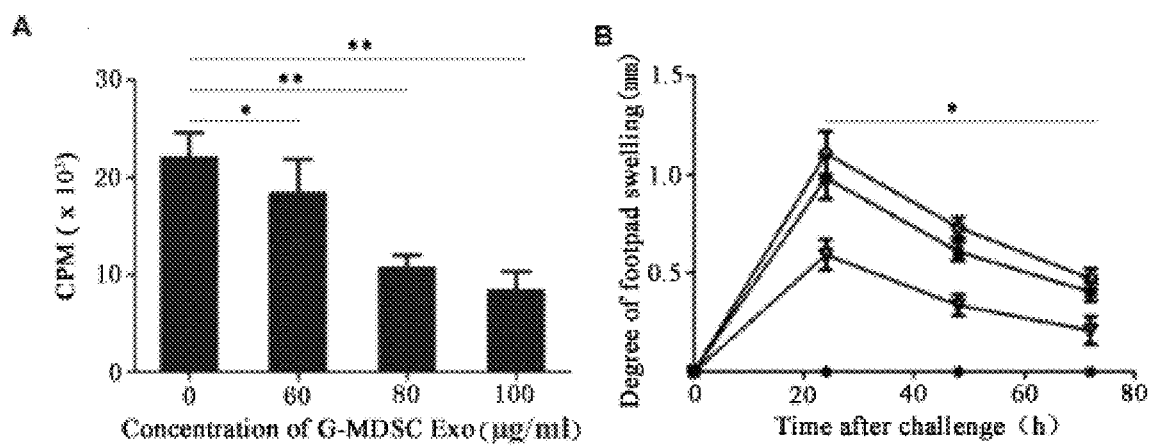
FIG. 3: G-MDSC exo suppresses CD4+ T cell proliferation. A: Effect of G-MDSC exo on suppressing CD4+ T cell proliferation measured by [3H]-thymidine incorporation method through in vitro observation; B: Effects of G-MDSC exo on suppressing the DTH model through in vivo observation.

FIG. 3 shows the result of G-MDSC exo inhibiting $CD4^+$ T cells, wherein, FIG. 3A shows the effect of G-MDSC exo on $CD4^+$ T cell proliferation observed by 3H-TdR incorporation method. The result shows that G-MDSC exo suppress $CD4^+$ T cell proliferation in dose-dependent manner. FIG. 3B shows the effect of G-MDSC exo on delayed type hypersensitivity observed by the DTH model. Swelling degree of footpad was measured after OVA-stimulating 24 h, 36 h, and 72 h. The results show that the footpad thickness in G-MDSC exo treatment group is lower than that in other groups. The results show that G-MDSC exo can suppress DTH reaction in vivo.

Example 5: G-MDSC Exo Promote Cell Proliferation from $CD4^+$ T Cells to Treg Induced by TGF-β in Dose-Dependent Manner The magnetic beads sorting of $CD4^+$ T cells was same the as example 4. $2\times10^6$/ml $CD4^+$ T cells in 1 ml cell culture medium were inoculated in 24-well plate and TGF-β inducing polarization of $CD4^+$ T cells to Treg, adding different dose of G-MDSC exo under the presence of anti-CD3 mAb and anti-CD28 mAb. $CD25^+Foxp3^+$ T cells were analyzed by FACS after culturing for 3 days. The result shows that, G-MDSC can promote cell proliferation from $CD4^+$ T cells to Treg induced by TGF-β (FIG. 4A) in dose-dependent manner (FIG. 4B).

Figure 4:
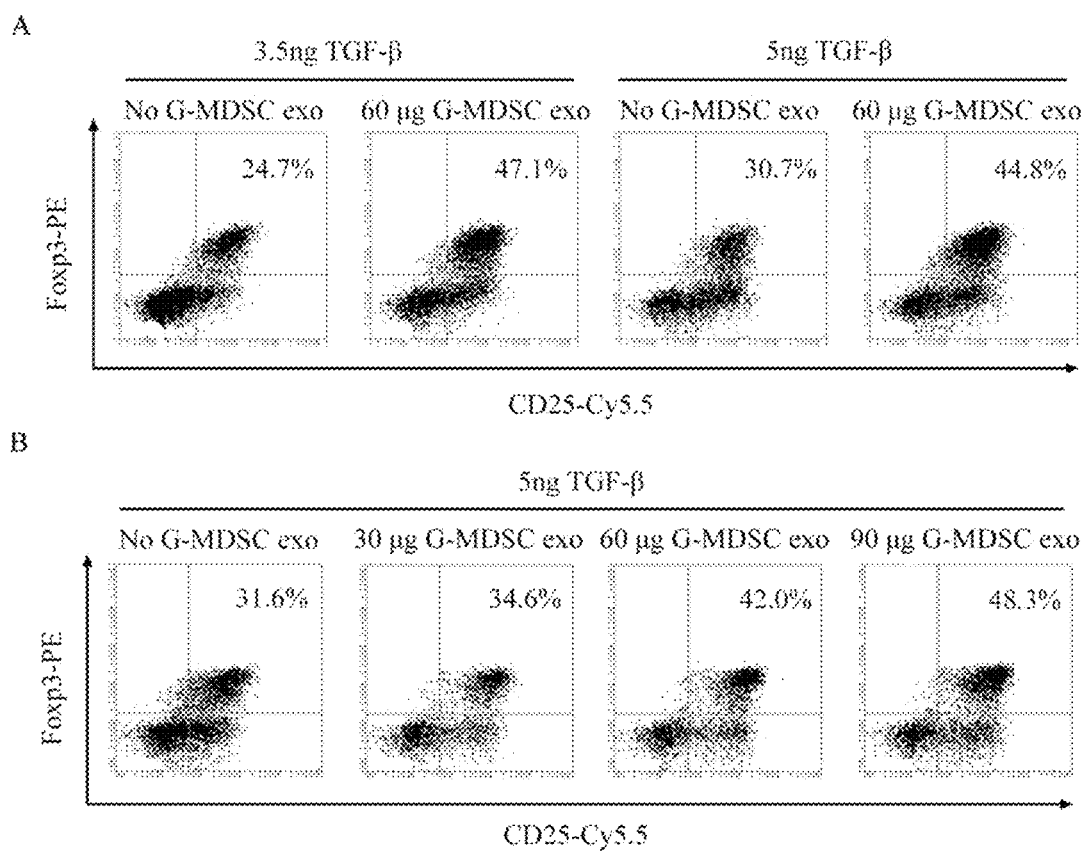
FIG. 4: G-MDSC exo promotes the expansion of CD4+ T cells to Tregs cells induced by TGF-β in a dose-dependent manner. Figure A shows G-MDSC exo promotes the expansion of CD4+ T cells to Tregs cells induced by TGF-β of different concentration. Figure B shows G-MDSC exo promotes the expansion of CD4+ T cells to Tregs cells induced by TGF-β in a dose-dependent manner.

FIG. 4 shows the result of G-MDSC exo promote cell proliferation from $CD4^+$ T cells to Treg induced by TGF-β in dose-dependent manner. FIG. 4A shows G-MDSC exo promote cell proliferation from $CD4^+$ T cells to Treg induced by TGF-β at different concentration The results show that G-MDSC exo can promote Treg proliferation from $CD4^+$ T cells under different doses of TGF-β. FIG. 4B shows G-MDSC exo promote cell proliferation from CD4+ T cells to Treg cells induced by TGF-β in dose-dependent manner. These results show that Treg proliferation induced by TGF-β is increased as the concentrations of G-MDSC exo increased.

Example 6: Treatment Efficacy of G-MDSC Exo on IBD Mouse (1) Preparation of 2.5% DSS and induction of inflammatory bowel disease: 25 g of Dextran Sulfate Sodium (DSS)

was dissolved in 1 L of double distilled H$_2$O and cooled after autoclaving 6-8 w male C57BL/6 mouse continuously drink 2.5% DSS solution for 9 days in free way to induce IBD.

(2) Mice are divided into four groups (6 mice per group) as follows:

Normal control group (NC): Mouse drinks double distilled water freely.

IBD group: Mouse drink 2.5% DSS solution without any other treatment.

Neu exo treatment group: Mice were treated with Neu exo through intraperitoneal injection (30 μg/mouse) on days 2, 4, and 6 after DSS drinking.

G-MDSC exo treatment group: Mice were treated with G-MDSC exo through intraperitoneal injection (30 μg/mouse) on days 2, 4, and 6 after DSS drinking.

Note: The day when drinking DSS is counted as day 0.

(3) Assessing IBD progression: the weight, stool property and hematochezia were monitored daily and graded DAI. Scoring criteria are as follows:

Weight change: <1% is 0 point, 1-5% is 1 point, 5-10% is 2 points, 10-15% is 3 points, >15% is 4 points;

Stool: normal is 0 point, loose stool is 2 points, shapeless diarrhea is 4 points;

Hematochezia: no is 0 point, visible blood is 4 points;

The sum of the points in each group divided by 3 is the final score.

(4) Observe colon specimens: Mouse were sacrificed on day 9 after inducing IBD disease by eye bloodletting, the abdominal cavity of mouse was opened, colon tissue between the end of anus rectum and distal end of caecum was isolated, and then the extent of swelling and the length of colon tissues were observed.

(5) Pathology analysis of colon tissue of mouse in all groups: Colon tissue between the end of anus rectum and distal end of caecum is isolated, the colons were fixed in 10% formalin solution, paraffin-embedded and stained with hematoxylin and eosin (H&E), and the pathological damage and degree of inflammation was observed under a microscope.

(6) Experimental results: Evaluate the disease of the colon of mouse in different groups through scoring of weight loss, stool property and hematochezia, the damage of the colon of mouses in all groups is observed by observing the outward appearance of colon, colon histopathological staining. The results showed that the clinical disease score of G-MDSC exo-treatment mouse is significantly lower (FIG. 5A), as well as decreased swelling and shorten of colon (FIG. 5B), and decreased histological damage, inflammatory cell infiltration and range of inflammatory damage (FIG. 5C).

Figure 5:
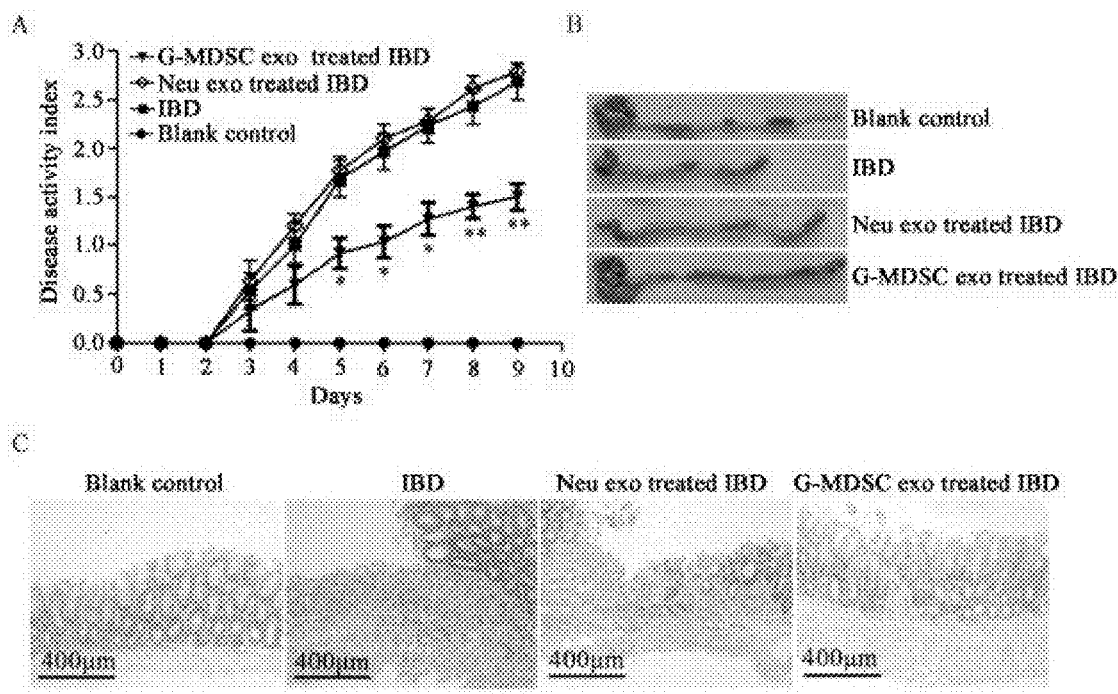
FIG. 5: The protective effect of G-MDSC exo to IBD mouse. A: Effect of G-MDSC exo on the disease progression of IBD mouse; B: Effect of G-MDSC exo on the colon tissues of IBD mouse; C: Effect of G-MDSC exo on colonic inflammation of IBD mouse.

FIG. 5 shows the protective role of G-MDSC exo in IBD mouse. The effect of G-MDSC exo on IBD disease progression is shown in FIG. 5A. The disease progression was scored by body weight, stool property and hematochezia situation. The result shows that the clinical score of mouse in G-MDSC exo-treatment group was lower than IBD group or Neu exo-treatment group. Moreover, this difference is statistically significant (P<0.05) (FIG. 5A). The effect of G-MDSC exo on the colon tissues of IBD mouse is shown in FIG. 5B. The degree of swelling and shorten of colon in G-MDSC exo-treatment group were lower than that of IBD group or Neu exo-treatment group (FIG. 5B). The effect of G-MDSC exo on degree of inflammation of colon tissue is shown in FIG. 5C. The inflammatory cell damage on colon tissue in G-MDSC exo-treatment group are lower than that in IBD mouse or Neu exo-treatment group through observing the pathological staining of colon tissue of mice in all groups (FIG. 5C). These results show that G-MDSC exo have protection for IBD mice.

Example 7: The Therapeutic Effect of G-MDSC Exo on CIA Mouse

Figure 6:
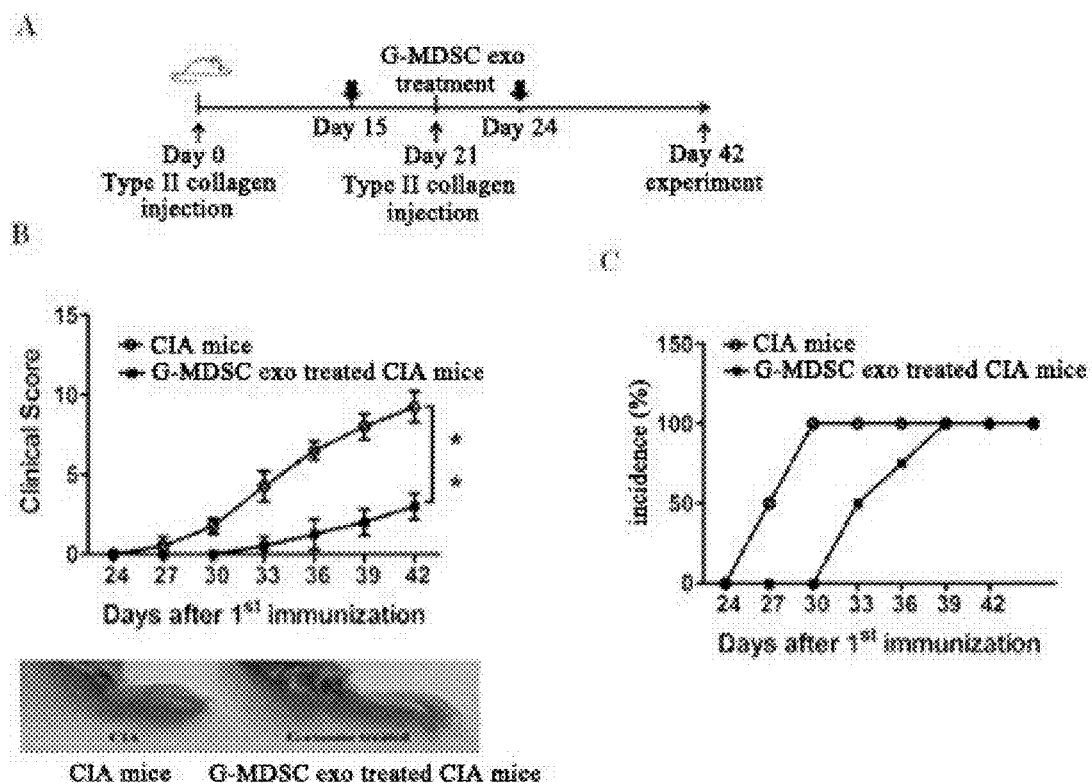
FIG. 6: The protective effect of G-MDSC exo on CIA mouse. A: Experimental flow diagram of CIA mouse intervened with G-MDSC exo. B: Effects of G-MDSC exo on disease scores of paw swelling in CIA mouse; C: Effects of G-MDSC exo on disease progression of CIA mouse.

The therapeutic effect of G-MDSC exo on CIA mouse: Mice were treated intravenously on tail with G-MDSC exo on the 18 days and 24 days after first immunization, the flowchart is shown in FIG. 6A. We found that the severity of arthritis was significantly reduced in mouse treated with G-MDSC exo (FIG. 6B), and the time of onset is significantly delayed (FIG. 6C). As shown in FIG. 6B, the swelling could be observed on days 27 after the initial immunization in untreated group, and the same case in G-MDSC exo treated group was observed on days 33. In addition, on days 42 after immunization, the joint score was up to 10 in untreated group, while the score of G-MDSC exo treated group was only about 4.

Example 8: G-MDSC Exo Carrying Arg-1 Play an Important Role in Attenuating Autoimmune Diseases (1) The activity detection of Arg-1 in G-MDSC exo and inhibition effect of nor-NOHA on the Arg-1 activity in G-MDSC exo: The sorted G-MDSCs are same to example 1. Inoculate 2×10$^6$ G-MDSCs per well in 24 well plate, and add 1 ml of RPMI-1640 medium and culture at 37° C., 5% CO$_2$ for 16 h. The culture supernatant is collected and used for preparing G-MDSC exo, then the G-MDSC exo was lysed (the same with example 2), and the G-MDSC exo activity was measured with the arginase assay kit from eBioscience company. 5 mg of nor-NOHA powder was dissolved with 1 ml of DMSO, 5 mg/ml nor-NOHA solution is prepared. Experimental groups were treated as follows:

G-MDSC group: G-MDSCs were cultured, and cells are collected.

(G-MDSC+DMSO) group: G-MDSC is cultured after adding 7W of DMSO, and cells were collected.

(G-MDSC+NN) group: G-MDSC is cultured after adding 7W of nor-NOHA, and cells were collected.

G-MDSC exo group: G-MDSC is cultured, culture supernatant was collected.

(G-MDSC+DMSO) exo group: G-MDSC is cultured after adding 7W of DMSO, culture supernatant was collected.

(G-MDSC+NN) exo group: G-MDSC is cultured after adding 7W of nor-NOHA, culture supernatant was collected.

The result shows that Arg-1 is contained in G-MDSC exo (FIG. 7A), and Arg-1 activity could be inhibited by NN.

(2) G-MDSC exo plays a protective role in autoimmune disease by Arg-1 therein. The present example observes that Arg-1 plays an important role in protecting IBD mediated by G-MDSC exo through IBD model. According to the requirement of experiment, the IBD mice are divided into Neu exo treatment group, G-MDSC exo treatment group, (G-MDSC+NN) exo treatment group, and (G-MDSC+DMSO) exo treatment group. The method of configuring the model, treating method and observing index are the same with example 5.

Figure 7:
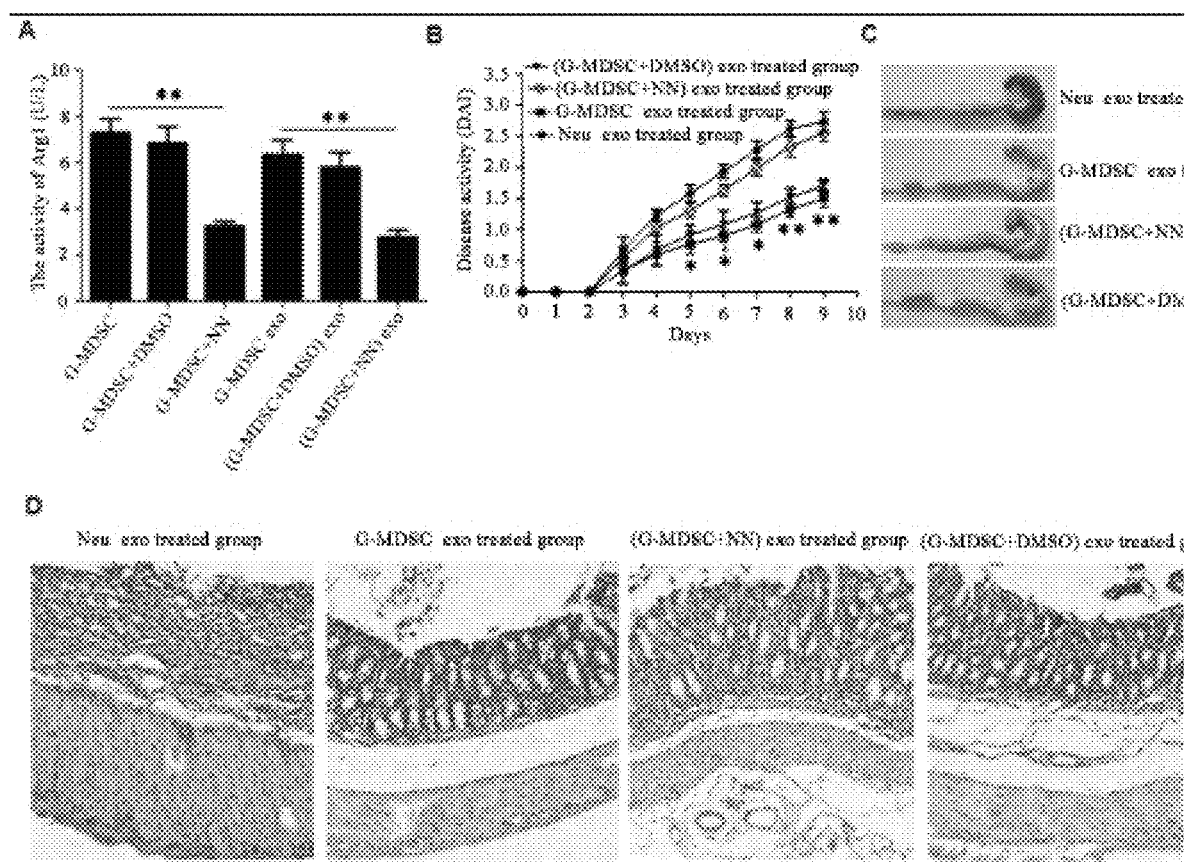
FIG. 7: Arginase (Arg)-1 carried by G-MDSC exo plays an important role on alleviating autoimmune diseases. A: Detection result of Arg-1 activity in G-MDSC exo and the suppression on Arg-1 activity by Arg-1 inhibitor nor-NOHA.

The results show that Arg-1 involves in the protective role of G-MDSC exo in autoimmune disease. FIG. 7B shows that the effects of (G-MDSC+NN) exo treatment group on disease progression of IBD mouse, clinic score of (G-MDSC+NN) exo treatment group is obviously higher than that of G-MDSC exo treatment group by scoring of weight change, stool property and hematochezia. The difference was statistically significant. FIG. 7C shows the effect of (G-MDSC+ NN) exo on the colon tissues of IBD mouse. The result shows that the degree of swelling and shortening process in (G-MDSC+NN) exo-treatment group are obviously higher than that in G-MDSC exo-treatment group. FIG. 7D shows the effect of (G-MDSC+NN) exo on the inflammation of colon tissues of IBD mouse. The degree of inflammatory cell damage on colon tissue and inflammatory infiltration in (G-MDSC+NN) exo-treatment group are more severe than that in G-MDSC exo-treatment group. These results strongly supported that Arg-1 played an important role in G-MDSC exo mediated protective roles in autoimmune diseases.

The invention claimed is:

1. A method of-treating a patient with an autoimmune disease comprising isolating G-MDSCs from cancer individuals or autoimmune disease individuals to obtain an isolated G-MDSC cell population having a purity of greater than 95%, culturing said G-MDSC cell population and isolating exosomes from the culture supernatant to provide G-MDSC derived exosomes, and administering to the patient an effective amount of said G-MDSC derived exosomes, wherein the exosomes are membrane vesicles containing the lipid component of cell membrane of derived sources, the exosomes also have nonspecific components of G-MDSCs and specific active components including protein and nucleic acid in G-MDSCs, and are composite informosomes of subcellular structure for intercellular information transmission, and wherein the exosomes contain Arg-1 and exhibit immunosuppressive properties.

2. The method according to claim 1, wherein, the autoimmune disease is inflammatory bowel disease.

3. The method according to claim 1, wherein, the autoimmune disease is autoimmune arthritis.

4. A method of treating a patient having an autoimmune disease, the method comprising:
isolating G-MDSCs from cancer individuals or autoimmune disease individuals to obtain an isolated G-MDSC cell population having a purity of greater than 95%, culturing said G-MDSC cell population and isolating exosomes from the culture supernatant to provide G-MDSC derived exosomes, and administering to the patient an effective amount of said G-MDSC derived exosomes, wherein the exosomes have circular or elliptic micro-capsule structure with complete envelope, and an intracavity having low electron density components, the exosomes also having a diameter of 40-100 nm and carrying biologically active ingredients, wherein the exosomes are membrane vesicles containing the lipid component of cell membrane of derived sources, the exosomes also have nonspecific components of G-MDSCs and specific active components including protein and nucleic acid in G-MDSCs, and are composite informosomes of subcellular structure for intercellular information transmission, and wherein the exosomes contain Arg-1 and exhibit immunosuppressive properties.

5. The method according to claim 4, wherein, the autoimmune disease is inflammatory bowel disease.

6. The method according to claim 4, wherein, the autoimmune disease is autoimmune arthritis.

7. A method of treating a patient having a disease caused by delayed type hypersensitivity reaction comprising:
isolating G-MDSCs from cancer individuals or autoimmune disease individuals to obtain an isolated G-MDSC cell population having a purity of greater than 95%, culturing said G-MDSC cell population and isolating exosomes from the culture supernatant to provide G-MDSC derived exosomes, and administering to the patient an effective amount of said G-MDSC derived exosomes, wherein the exosomes are membrane vesicles containing the lipid component of cell membrane of derived sources, the exosomes also have nonspecific components of G-MDSCs and specific active components including protein and nucleic acid in G-MDSCs, and are composite informosomes of subcellular structure for intercellular information transmission, and wherein the exosomes contain Arg-1 and exhibit immunosuppressive properties.

* * * * *